United States Patent [19]
Lechner et al.

[11] Patent Number: 5,459,036
[45] Date of Patent: Oct. 17, 1995

[54] EXTRACELLULAR SIGNAL-REGULATED KINASE, SEQUENCES, AND METHODS OF PRODUCTION AND USE

[75] Inventors: Cornelia Lechner; Niels P. H. Møller; Axel Ullrich, all of München, Germany

[73] Assignee: Max-Planck-Gesellschaft Zur Forderung Der Wissenschaften E.V., Munich, Germany

[21] Appl. No.: 29,404

[22] Filed: Mar. 19, 1993

[51] Int. Cl.$^6$ .............................. C12Q 1/68; C07H 21/04
[52] U.S. Cl. .................. 435/6; 435/240.2; 435/252.3; 435/320.1; 536/23.5; 536/24.31
[58] Field of Search ............... 435/6, 320.1, 240.2, 435/252.3; 536/23.5, 24.31

[56] References Cited

U.S. PATENT DOCUMENTS 5,219,748  6/1993  Yoshitaka et al. ............... 435/194

FOREIGN PATENT DOCUMENTS

WO91/19008  12/1991  WIPO .
WO92/13001  8/1992  WIPO .
WO92/21641  12/1992  WIPO .
WO92/21660  12/1992  WIPO .

OTHER PUBLICATIONS

Owaki et al., "Extracellular Signal-Regulated Kinases in T Cell Characterization of the Human ERK1 and ERK2 cDNAs[1,2]", 182 *Biochem. and Biophys. Res. Comm.* 1416, 1992.

Ahn, N. G. et al., "Identification of multiple epidermal growth factor-stimulated protein serine/threonine kinases from Swiss 3T3 cells", *J. Biol. Chem.* 265(20):11487–11494 (Jul. 15, 1990).

Ahn, N. G. and Krebs, E. G., "Evidence for an epidermal growth factor-stimulated protein kinase cascade in Swiss 3T3 cells", *J. Biol. Chem.* 265(20):11495–11501 (Jul. 15, 1990).

Ballou, L. M. et al., "Protein phosphatase 2A inactivates the mitogen-stimulated S6 kinase from Swiss mouse 3T3 cells", *J. Biol. Chem.* 263(3):1188–1194 (Jan. 25, 1988).

Borthwick, A. C. et al., "Protein-serine kinase from rat epididymal adipose tissue which phosphorylates and activates acetyl-CoA carboxylase", *Biochem. J.* 270:795–801 (1990).

Boulton, T. G. et al., "ERKs: a family of protein-serine/threonine kinases that are activated and tyrosine phosphorylated in response to insulin and NGF", *Cell* 65:663–675 (May 17, 1991).

Boulton, T. G. et al., "Purification and properties of extracellular signal-regulated kinase 1, an insulin-stimulated microtubule-associated protein 2 kinase", *Biochemistry* 30:278–286 (1991).

Boulton, T. G. and Cobb, M. H., "Identification of multiple extracellular signal-regulated kinases (ERKs) with antipeptide antibodies", *Cell Regul.* 2:357–371 (May 1991).

Boulton, T. G. et al., "An insulin-stimulated protein kinase similar to yeast kinases involved in cell cycle control", *Science* 249:64–67 (Jul. 6, 1990).

Chung, J. et al., "Mitogen-activated Swiss mouse 3T3 RSK kinases I and II are related to pp44$^{mpk}$ from sea star oocytes and participate in the regulation of pp90$^{rsk}$ activity", *Proc. Natl. Acad. Sci. USA* 88:4981–4985 (Jun. 1991).

Cicirelli, M. F. et al., "Activation of multiple protein kinases during the burst in protein phosphorylation that precedes the first meiotic cell division in *Xenopus* oocytes", *J. Biol. Chem.* 263(4):2009–2019 (Feb. 5, 1988).

Cobb, M. H. et al., "Extracellular signal-regulated kinases: ERKs in progress", *Cell Regulation* 2:965–978 (Dec. 1991).

Cooper, J. A. et al., "Diverse mitogenic agents induce the phosphorylation of two related 42,000-dalton proteins on tyrosine in quiescent chick cells", *Mol. Cell. Biol.* 4(1):30–37 (Jan. 1984).

Dent, P. et al., "The Molecular mechanism by which insulin stimulates glycogen synthesis in mammalian skeletal muscle", *Nature* 348:302–308 (Nov. 22, 1990).

Duerr, B. et al., "MsERK1: a mitogen-activated protein kinase from a flowering plant", *The Plant Cell* 5:87–96 (Jan. 1993).

Ferrell, J. E., Jr. and Martin, G. S., "Identification of a 42-kilodalton phosphotyrosyl protein as a serine(threonine) protein kinase by renaturation", *Mol. Cell. Biol.* 10(6):3020–3026 (Jun. 1990).

Gotoh, Y. et al., "*Xenopus* M phase MAP Kinase: isolation of its cDNA and activation by MPF", *EMBO J.* 10(9):2661–2668 (1991).

Gotoh, Y. et al., "In vitro effects on microtubule dynamics of purified *Xenopus* M phase-activated MAP kinase", *Nature* 349:251–254 (Jan. 17, 1991).

Gregory, J. S. et al., "An insulin-stimulated ribosomal protein S6 kinase from rabbit liver", *J. Biol. Chem.* 264(31):18397–18401 (Nov. 5, 1989).

Hanks, S. K. et al., "The protein kinase family: conserved features and deduced phylogeny of the catalytic domains", *Science* 241:42–52 (Jul. 1, 1988).

(List continued on next page.)

Primary Examiner—Margaret Parr
Assistant Examiner—Kenneth R. Horlick
Attorney, Agent, or Firm—Lyon & Lyon

[57] ABSTRACT

The present invention relates, in general, to an extracellular signal regulated kinase, ERK-5. In particular, the present invention relates to nucleic acid molecules coding for ERK-5; ERK-5 polypeptides; recombinant nucleic acid molecules; cells containing the recombinant nucleic acid molecules; antisense ERK-5 nucleic acid constructs; antibodies having binding affinity to an ERK-5 polypeptide; hybridomas containing the antibodies; nucleic acid probes for the detection of ERK-5 nucleic acid; a method of detecting ERK-5 nucleic acid or polypeptide in a sample; kits containing nucleic acid probes or antibodies; a method of detecting a compound capable of binding to ERK-5 or a fragment thereof; a method of detecting an agonist or antagonist of ERK-5 activity; a method of agonizing or antagonizing ERK-5 associated activity in a mammal; and a pharmaceutical composition comprising an ERK-5 agonist or antagonist.

18 Claims, 8 Drawing Sheets

OTHER PUBLICATIONS

Her, J. et al., "Sequence of pp42/MAP kinase, a serine/threonine kinase regulated by tyrosine phosphorylation", *Nucleic Acids Res.* 19(13):3743 (1991).

Horshi, M. et al., "Activation of a $Ca^{2+}$-inhibitable protein kinase that phosphorylates microtubule–associated protein 2 in vitro by growth factors, phorbol esters, and serum in quiescent cultured human fibroblasts", *J. Biol. Chem.* 263(11):5396–5401 (Apr. 15, 1988).

Kyriakis, J. M. et al., "pp54 microtubule–associated protein–2 kinase requires both tyrosine and serine/threonine phosphorylation for activity", *J. Biol. Chem.* 266(16):10043–10046 (Jun. 5, 1991).

Kyriakis, J. M. and Avruch, J., "pp54 microtubule–associated protein 2 kinase", *J. Biol. Chem.* 265(28):17355–17363 (Oct. 5, 1990).

Northwood, I. C. et al., "Isolation and characterization of two growth factor–stimulated protein kinases that phosphorylate the epidermal growth factor receptor at threonine 669", *J. Biol. Chem.* 266(23):15266–15276 (Aug. 15, 1991).

Posada, J. et al., "Tyrosine phosphorylation and activation of homologous protein kinases during oocyte maturation and mitogenic activation of fibroblasts", *Mol. Cell. Biol.* 11(5):2517–2528 (May 1991).

Ray, L. B. and Sturgill, T. W., "Characterization of insulin–stimulated microtubule–associated protein kinase", *J. Biol. Chem.* 263(25):12721–12727 (Sep. 5, 1988).

Ray, L. B. and Sturgill, T. W., "Rapid stimulation by insulin of a serine/threonine kinase in 3T3-L1 adipocytes that phosphorylates microtubule–associated protein 2 in vitro", *Proc. Natl. Acad. Sci. USA* 84:1502–1506 (Mar. 1987).

Ray, L. B. and Sturgill, T. W., "Insulin–stimulated microtubule–associated protein kinase is phosphorylated on tyrosine and threonine in vivo", *Proc. Natl. Acad. Sci. USA* 85:3753–3757 (Jun. 1988).

Rossomando, A. J. et al., "Evidence that pp42, a major tyrosine kinase target, is a mitogen–activates serine/threonine protein kinase", *Proc. Natl. Acad. Sci. USA* 86:6940–6943 (Sep. 1989).

Sanghera, J. S. et al., "Identification of the sites in myelin basic protein that are phosphorylated by meiosis–activated protein kinase $p44^{mpk}$", *FEBS Lett.* 273:223–226 (Oct. 1990).

Seger, R. et al., "Microtubule–associated protein 2 kinases, ERK1 and ERK2, undergo autophosphorylation on both tyrosine and threonine residues: implications for their mechanism of activation", *Proc. Natl. Acad. Sci. USA* 88:6142–6146 (Jul. 1991).

Sturgill, T. W. et al., "Insulin–stimulated MAP–2 kinase phosphorylates and activates ribosomal protein S6 kinase II", *Nature* 334:715–718 (Aug. 25, 1988).

Sturgill, T. W. and Wu, J., "Recent progress in characterization of protein kinase cascades for phosphorylation of ribosomal protein S6", *Biochim. Biophys. Acta* 1092:350–357 (1991).

Tsao, H. and Greene, L. A., "The roles of macromolecular synthesis and phosphorylation in the regulation of a protein kinase activity transiently stimulated by nerve growth factor", *J. Biol. Chem.* 266(20):12981–12988 (Jul. 15, 1991).

FIG. 1a.

```
    1   ggctctgcggggtgggcagctcccgggcctgccatgagctctccgccgcccggxggcagt
        ----------+---------+---------+---------+---------+---------+  60
        ccgagacgccccacccgtcgagggcccggacggtactcgagaggcggcgggccxccgtca
                                              M  S  S  P  P  P  G  G  S  -

61   ggcttttaccgccaggaggtgaccaagacggcctgggaggtgcgcgccgtgtaccgggac
        ----------+---------+---------+---------+---------+---------+ 120
        ccgaaaatggcggtcctccactggttctgccggaccctccacgcgcggcacatggccctg
  a      G  F  Y  R  Q  E  V  T  K  T  A  W  E  V  R  A  V  Y  R  D  -

121   ctgcagcccgtgggctcgggcgcctacggcgcggtgtgctcggccgtggacggccgcacc
        ----------+---------+---------+---------+---------+---------+ 180
        gacgtcgggcacccgagcccgcggatgccgcgccacacgagccggcacctgccggcgtgg
  a      L  Q  P  V  G  S  G  A  Y  G  A  V  C  S  A  V  D  G  R  T  -

181   ggcgctaaggttgccatcaagaagctgtatcggcccttccagtccgagctgttcgccaag
        ----------+---------+---------+---------+---------+---------+ 240
        ccgcgattccaacggtagttcttcgacatagccgggaaggtcaggctcgacaagcggttc
  a      G  A  K  V  A  I  K  K  L  Y  R  P  F  Q  S  E  L  F  A  K  -

241   ctcgcctaccgcgagctgcgcctgctcaagcacatgcgccacgagaacgtgatcgggctg
        ----------+---------+---------+---------+---------+---------+ 300
        gagcggatggcgctcgacgcggacgagttcgtgtacgcggtgctcttgcactagcccgac
  a      L  A  Y  R  E  L  R  L  L  K  H  M  R  H  E  N  V  I  G  L  -

301   ctggacgtattcactcctgatgagaccctggatgacttcacggacttttacctggtgatg
        ----------+---------+---------+---------+---------+---------+ 360
        gacctgcataagtgaggactactctgggacctactgaagtgcctgaaaatggaccactac
  a      L  D  V  F  T  P  D  E  T  L  D  D  F  T  D  F  Y  L  V  M  -

361   ccgttcatgggcaccgacctgggcaagctcatgaaacatgagaagctaggcgaggaccgg
        ----------+---------+---------+---------+---------+---------+ 420
        ggcaagtacccgtggctggacccgttcgagtactttgtactcttcgatccgctcctggcc
  a      P  F  M  G  T  D  L  G  K  L  M  K  H  E  K  L  G  E  D  R  -

421   atccagttcctcgtgtaccagatgatgaaggggctgaggtatatccacgctgccggcatc
        ----------+---------+---------+---------+---------+---------+ 480
        taggtcaaggagcacatggtctactacttccccgactccatataggtgcgacggccgtag
  a      I  Q  F  L  V  Y  Q  M  M  K  G  L  R  Y  I  H  A  A  G  I  -

481   atccacagagacctgaagcccggcaacctggctgtgaacgaagactgtgagctgaagatc
        ----------+---------+---------+---------+---------+---------+ 540
        taggtgtctctggacttcgggccgttggaccgacacttgcttctgacactcgacttctag
  a      I  H  R  D  L  K  P  G  N  L  A  V  N  E  D  C  E  L  K  I  -
```

FIG. 1b.

```
      ctggacttcggcctggccaggcaggcagacagtgagatgactgggtacgtggtgacccgg
541   ----------+----------+----------+----------+----------+----------+  600
      gacctgaagccggaccggtccgtccgtctgtcactctactgacccatgcaccactgggcc a     L  D  F  G  L  A  R  Q  A  D  S  E  M  T  G  Y  V  V  T  R   - tggtaccgggctcccgaggtcatcttgaattggatcgcgtacacgcagacggtggacatc
601   ----------+----------+----------+----------+----------+----------+  660
      accatggcccgagggctccagtagaacttaacctagcgcatgtgcgtctgccacctgtag a     W  Y  R  A  P  E  V  I  L  N  W  I  A  Y  T  Q  T  V  D  I   - tggtctgtgggctgcatcatggcggagatgatcacaggcaagacgctgttcaagggcagc
661   ----------+----------+----------+----------+----------+----------+  720
      accagacacccgacgtagtaccgcctctactagtgtccgttctgcgacaagttcccgtcg a     W  S  V  G  C  I  M  A  E  M  I  T  G  K  T  L  F  K  G  S   - gaccacctggaccagctgaaggagatcatgaaggtgacggggacgcctccggctgagttt
721   ----------+----------+----------+----------+----------+----------+  780
      ctggtggacctggtcgacttcctctagtacttccactgcccctgcggaggccgactcaaa a     D  H  L  D  Q  L  K  E  I  M  K  V  T  G  T  P  P  A  E  F   - gtgcagcggctgcagagcgatgaggccaagaactacatgaagggcctccccgaattggag
781   ----------+----------+----------+----------+----------+----------+  840
      cacgtcgccgacgtctcgctactccggttcttgatgtacttcccggaggggcttaacctc a     V  Q  R  L  Q  S  D  E  A  K  N  Y  M  K  G  L  P  E  L  E   - aagaaggattttgcctctatcctgaccaatgcaagccctctggctgtgaacctcctggag
841   ----------+----------+----------+----------+----------+----------+  900
      ttcttcctaaaacggagataggactggttacgttcgggagaccgacacttggaggacctc a     K  K  D  F  A  S  I  L  T  N  A  S  P  L  A  V  N  L  L  E   - aagatgctggtgctggfcgcggacatcaggttgactgcaggcgagtttctttcccatccc
901   ----------+----------+----------+----------+----------+----------+  960
      ttctacgaccacgacctgcgcctgtagtccaactgacgtccgctcaaagaaagggtaggg a     K  M  L  V  L  D  A  D  I  R  L  T  A  G  E  F  L  S  H  P   - tacttcgagtccctgcacgacacggaagatgagccccaggtccagaagtatgatgactcc
961   ----------+----------+----------+----------+----------+----------+  1020
      atgaagctcagggacgtgctgtgccttctactcggggtccaggtcttcatactactgagg a     Y  F  E  S  L  H  D  T  E  D  E  P  Q  V  Q  K  Y  D  D  S   - tttgactactttgaccgcacactggatgaatggaagccgtgttacttacaaagaggtgct
1021  ----------+----------+----------+----------+----------+----------+  1080
      aaactgatgaaactggcgtgtgacctacttaccttcggcacaatgaatgtttctccacga a     F  D  Y  F  D  R  T  L  D  E  W  K  P  C  Y  L  Q  R  G  A   -
```

FIG. 1c.

```
       cagcttcaagcctcccccggcagctgggggccagggtctccaaggagacgcctctgtgaag
1081   ----------+---------+---------+---------+---------+---------+ 1140
       gtcgaagttcggagggggccgtcgaccccccggtcccagagaggttcctctgcggagacacttc
``` a      Q  L  Q  A  S  P  A  A  G  G  Q  G  L  Q  G  D  A  S  V  K   -

```
       atctctgggctccggggtggcagtgaggaccaccttcaccttccacctgagaggggactc
1141   ----------+---------+---------+---------+---------+---------+ 1200
       tagagacccgaggccccaccgtcactcctggtggaagtggaaggtggactctcccctgag
``` a      I  S  G  L  R  G  G  S  E  D  H  L  H  L  P  P  E  R  G  L   -

```
       tcgttgccaccttgaccttggctggggcttgcatcccaaggcatccatcagagcagacgc
1201   ----------+---------+---------+---------+---------+---------+ 1260
       agcaacggtggaactggaaccgaccccgaacgtagggttccgtaggtagtctcgtctgcg
``` a      S  L  P  P  *                                                 -

EXTRACELLULAR SIGNAL-REGULATED KINASE, SEQUENCES, AND METHODS OF PRODUCTION AND USE

BACKGROUND OF THE INVENTION

1. Field of the Invention

The present invention relates, in general, to an extracellular signal regulated kinase, ERK-5. In particular, the present invention relates to nucleic acid molecules coding for ERK-5; ERK-5 polypeptides; recombinant nucleic acid molecules; cells containing the recombinant nucleic acid molecules; antisense ERK-5 nucleic acid constructs; antibodies having binding affinity to an ERK-5 polypeptide; hybridomas containing the antibodies; nucleic acid probes for the detection of ERK-5 nucleic acid; a method of detecting ERK-5 nucleic acid or polypeptide in a sample; kits containing nucleic acid probes or antibodies; a method of detecting a compound capable of binding to ERK-5 or a fragment thereof; a method of detecting an agonist or antagonist of ERK-5 activity; a method of agonizing or antagonizing ERK-5 associated activity in a mammal; a method of treating diabetes mellitus, skeletal muscle diseases, Alzheimer's disease, or peripheral neuropathies in a mammal with an agonist or antagonist of ERK-5 activity; and a pharmaceutical composition comprising an ERK-5 agonist or antagonist.

2. Background Information

Phosphorylation of serine/threonine residues on ribosomal protein S6 kinases (Ballou et al., *J. Biol. Chem.* 263:1188–1194 (1988)), phosphatase 1 G binding protein (Dent et al., *Nature* 348:302–308 (1990)), and acetyl coA-carboxylase (Borthwick et al., *Biochem. J.* 270:795–801 (1990)) occur in response to insulin and other extracellular cues. Ray and Sturgill, *Proc. Natl. Acad. Sci. USA* 84:1502–1506 (1987), Cicirelli et al., *J. Biol. Chem.* 263:2009–2019 (1988), and Hoshi et al., *J. Biol. Chem.* 263:5396–5401 (1988) have identified a micro tubule-associated protein 2 (MAP2)/myelin basic protein (MBP) kinase that in response to insulin contains phosphate on serine/threonine residues (Ray and Sturgill, *Proc. Natl. Acad. Sci. USA* 85:3753–3757 (1988); Boulton et al., *Cell* 65:663–675 (1991)). Ribosomal protein S6 kinase has been identified as one potential target for this kinase (Sturgill et al., *Nature* 334:715–718 (1988); Gregory et al., *J. Biol. Chem.* 264:18397–18401 (1989); Ahn and Krebs, *J. Biol. Chem.* 265:11495–11591 (1990)). Boulton et al., *Biochemistry* 30:278–286 (1991) and Boulton et al., *Science* 249:64–65 (1990) describe the purification and cloning of a MAP2/MBP kinase which they named extracellular signal-regulated kinase 1 (ERK-1). Using probes derived from ERK-1, two novel kinases were identified, ERK-2 and ERK-3 (Boulton and Cobb, *Cell Regulation* 2:357–371 (May 1991); Boulton et al., *Cell* 65:663–675 (May 17, 1991)). A fourth ERK has been briefly described (Cobb et al., *Cell Regulation* 2:965–978 (December 1991) and WO 91/19008 published Dec. 12, 1991).

The present invention provides a novel ERK, ERK-5. ERK-5 shows 61% similarity (38% identity) to the human ERK1 peptide sequence, 64% similarity to the rat ERK1 and ERK2 (39% and 37 % identity, respectively) and 55 % similarity to the rat ERK3 (30% identity).

SUMMARY OF THE INVENTION

The invention provides ERK-5.

The invention also provides an isolated nucleic acid molecule coding for a polypeptide comprising an amino acid sequence corresponding to ERK-5, or at least 9 contiguous amino acids thereof.

The invention further provides a substantially pure polypeptide comprising an amino acid sequence corresponding to ERK-5, or at least 9 contiguous amino acids thereof.

The invention also provides a nucleic acid probe for the detection of the presence of ERK-5 in a sample.

The invention further provides a method of detecting ERK-5 RNA in a sample.

The invention also provides a kit for detecting the presence of ERK-5 RNA in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a transcriptional region functional in a cell, a sequence complimentary to an RNA sequence encoding an amino acid sequence corresponding to the above-described polypeptide, and a transcriptional termination region functional in said cell.

The invention also provides a cell that contains the above-described recombinant nucleic acid molecule.

The invention further provides an organism that contains the above-described recombinant nucleic acid molecule.

The invention also provides an antibody having binding affinity to an ERK-5 polypeptide, or a binding fragment thereof.

The invention further provides a method of detecting an ERK-5 polypeptide in a sample.

The invention also provides a method of measuring the amount of ERK-5 in a sample.

The invention further provides a diagnostic kit comprising a first container means containing the above-described antibody, and a second container means containing a conjugate comprising a binding partner of said monoclonal antibody and a label.

The invention also provides a hybridoma which produces the above-described monoclonal antibody.

The invention further provides a method of detecting a compound capable of binding to ERK-5 or a fragment thereof.

The invention also provides a method of detecting an agonist or antagonist of ERK-5 activity.

The invention further provides a method of agonizing or antagonizing ERK-5 associated activity in a mammal.

The invention also provides a method of treating diabetes mellitus, skeletal muscle diseases, Alzheimer's disease, or peripheral neuropathies in a mammal with an agonist or antagonist of ERK-5 activity.

The invention further provides a pharmaceutical composition comprising an ERK-5 agonist or antagonist.

Further objects and advantages of the present invention will be clear from the description that follows.

BRIEF DESCRIPTION OF THE DRAWINGS

FIG. 1. Nucleotide (SEQ ID NO:1) and amino acid sequence (SEQ ID NO:2) of hERK5.

DEFINITIONS

Figure 2:
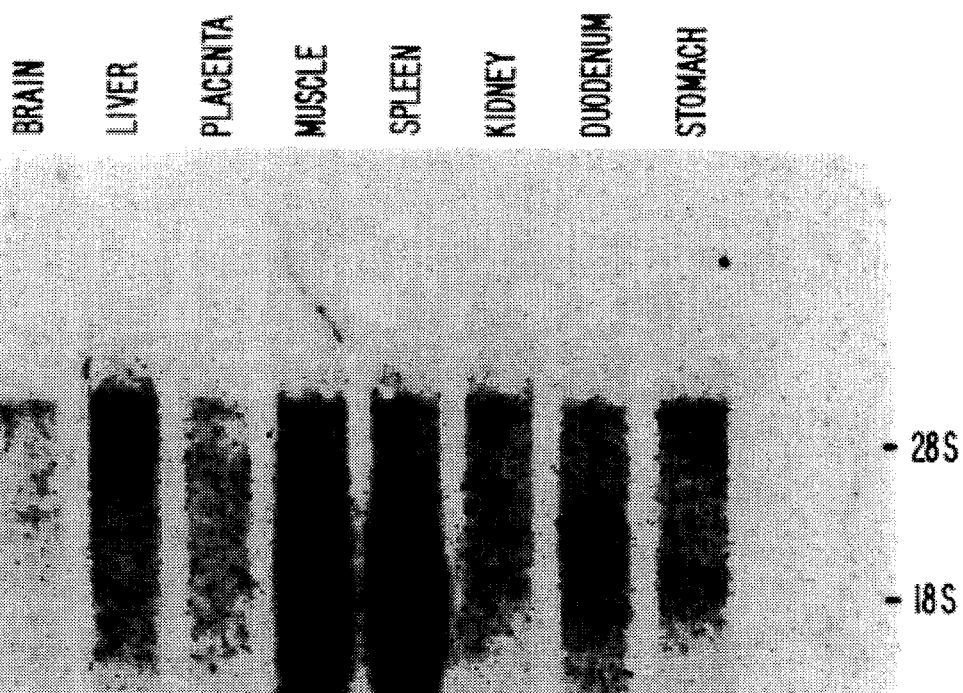
FIG. 2. Northern blot of brain, liver, placenta, muscle, spleen, kidney, duodenum, and stomach RNAs.

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule.

An "isolated nucleic acid molecule", as is generally understood and used herein, refers to a polymer of nucleotides, and includes but should not be limited to DNA and RNA.

DNA Segment.

A DNA segment, as is generally understood and used herein, refers to a molecule comprising a linear stretch of nucleotides wherein the nucleotides are present in a sequence that may encode, through the genetic code, a molecule comprising a linear sequence of amino acid residues that is referred to as a protein, a protein fragment or a polypeptide.

Gene.

A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA).

Recombinant nucleic acid molecules synthesized by reverse transcription of messenger RNA ("mRNA").

Structural Gene.

A DNA sequence that is transcribed into mRNA that is then translated into a sequence of amino acids characteristic of a specific polypeptide.

Restriction Endonuclease.

A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment.

The DNA molecules produced by digestion with a restriction endonuclease are referred to as restriction fragments. Any given genome may be digested by a particular restriction endonuclease into a discrete set of restriction fragments.

Agarose Gel Electrophoresis.

To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure.

The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization.

Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe.

To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer.

A molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Sequence Amplification.

A method for generating large amounts of a target sequence. In general, one or more amplification primers are annealed to a nucleic acid sequence. Using appropriate enzymes, sequences found adjacent to, or in between the primers are amplified.

Amplification Primer.

An oligonucleotide which is capable of annealing adjacent to a target sequence and serving as an initiation point for DNA synthesis when placed under conditions in which synthesis of a primer extension product which is complementary to a nucleic acid strand is initiated.

Vector.

A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. Markers, for example, are tetracycline resistance or ampicillin resistance. The words "cloning vehicle" are sometimes used for "vector."

Expression.

Expression is the process by which a structural gene produces a polypeptide. It involves transcription of the gene into mRNA, and the translation of such mRNA into polypeptide(s).

Expression Vector.

A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative.

A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Fragment.

A "fragment" of a molecule such as a protein or nucleic acid is meant to refer to any portion of the amino acid or nucleotide genetic sequence.

Variant.

A "variant" of a protein or nucleic acid is meant to refer to a molecule substantially similar in structure and biological activity to either the protein or nucleic acid, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog.

An "analog" of a protein or genetic sequence is meant to refer to a protein or genetic sequence substantially similar in function to a protein or genetic sequence described herein.

Allele.

An "allele" is an alternative form of a gene occupying a given locus on the chromosome.

Mutation.

A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

Species.

A "species" is a group of actually or potentially interbreeding natural populations. A species variation within a nucleic acid molecule or protein is a change in the nucleic acid or amino acid sequence that occurs among species and may be determined by DNA sequencing of the molecule in question.

Substantially Pure.

A "substantially pure" protein or nucleic acid is a protein or nucleic acid preparation that is generally lacking in other cellular components.

DETAILED DESCRIPTION OF THE INVENTION

Isolated Nucleic Acid Molecules Coding for ERK-5 Polypeptides, and Fragments Thereof.

In one embodiment, the present invention relates to an isolated nucleic acid molecule coding for a polypeptide having an amino acid sequence corresponding to ERK-5, or at least 9 contiguous amino acids thereof (preferably, at least 10, 15, 20, or 30 contiguous amino acids thereof). In one preferred embodiment, the isolated nucleic acid molecule comprises the sequences set forth in SEQ ID NO:1; allelic, mutant or species variation thereof, or at least 27 contiguous nucleotides thereof (preferably at least 30, 35, 40, or 50 contiguous nucleotides thereof). In another preferred embodiment, the isolated nucleic acid molecule encodes the amino acid sequence set forth in SEQ ID NO:2, or mutant or species variation thereof, or at least 9 contiguous amino acids thereof (preferably, at least 10, 15, 20, or 30 contiguous amino acids thereof).

Also included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the ERK-5 gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the ERK-5 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid.

In one aspect of the present invention, isolated nucleic acid molecules coding for polypeptides having amino acid sequences corresponding to ERK-5 are provided. In particular, the nucleic acid molecule may be isolated from a biological sample containing RNA or DNA.

The nucleic acid molecule may be isolated from a biological sample containing RNA using the techniques of cDNA cloning and subtractive hybridization as previously described (Birkenbach et al., *J. of Virology* 63:9:4079–4084). The nucleic acid molecule may also be isolated from a cDNA library using a homologous probe.

The nucleic acid molecule may be isolated from a biological sample containing genomic DNA or from a genomic library using techniques well known in the art. Suitable biological samples include, but are not limited to, blood, semen and tissue. The method of obtaining the biological sample will vary depending upon the nature of the sample.

One skilled in the art will realize that the human genome may be subject to slight allelic variations between individuals. Therefore, the isolated nucleic acid molecule is also intended to include allelic variations, so long as the sequence is a functional derivative of the ERK-5 gene.

One skilled in the art will realize that organisms other than humans may also contain ERK-5 genes (for example, eukaryotes; more specifically, mammals, birds, fish, and plants; more specifically, gorillas, rhesus monkeys, and chimpanzees). The invention is intended to include, but not be limited to, ERK-5 nucleic acid molecules isolated from the above-described organisms.

B. Synthesis of Nucleic Acid.

Isolated nucleic acid molecules of the present invention are also meant to include those chemically synthesized. For example, a nucleic acid molecule with the nucleotide sequence which codes for the expression product of an ERK-5 gene may be designed and, if necessary, divided into appropriate smaller fragments. Then an oligomer which corresponds to the nucleic acid molecule, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

II. Substantially Pure ERK-5 Polypeptides.

In another embodiment, the present invention relates to a substantially pure polypeptide having an amino acid sequence corresponding to ERK-5, or at least 9 contiguous amino acids thereof (preferably, at least 10, 15, 20, or 30 contiguous amino acids thereof). In a preferred embodiment, the polypeptide has the amino acid sequence set forth in SEQ ID NO:2, or mutant or species variation thereof, or at least 9 contiguous amino acids thereof (preferably, at least 10, 15, 20, or 30 contiguous amino acids thereof).

A variety of methodologies known in the art can be utilized to obtain the peptide of the present invention. In one embodiment, the peptide is purified from tissues or cells which naturally produce the peptide. Alternatively, the above-described isolated nucleic acid fragments could be used to expressed the ERK-5 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

III. A Nucleic Acid Probe for the Detection of ERK-5.

In another embodiment, the present invention relates to a nucleic acid probe for the detection of the presence of ERK-5 in a sample comprising the above-described nucleic acid molecules or at least 27 contiguous nucleotides thereof (preferably at least 30, 35, 40, or 50 thereof). In another preferred embodiment, the nucleic acid probe has the nucleic acid sequence set forth in SEQ ID NO:1 or at least 27 contiguous nucleotides thereof (preferably at least 30, 35, 40, or 50 thereof). In another preferred embodiment, the nucleic acid probe encodes the amino acid sequence set forth in SEQ ID NO:2 or at least 9 contiguous amino acids thereof.

The nucleic acid probe may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. *Molecular Cloning: A Laboratory Manual second edition,* edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to *PCR Protocols, A Guide to Methods and Applications,* edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual second edition,* edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of ERK-5 in a Sample.

In another embodiment, the present invention relates to a method of detecting the presence of ERK-5 in a sample comprising a) contacting said sample with the above-described nucleic acid probe, under conditions such that hybridization occurs, and b) detecting the presence of said probe bound to said nucleic acid molecule. One skilled in the art would select the nucleic acid probe according to techniques known in the art as described above. Samples to be tested include but should not be limited to RNA samples of human tissue.

ERK-5 has been found to be predominantly expressed in muscle. Accordingly, ERK-5 probes may be used detect the presence of RNA from muscle in a sample. Further, altered expression levels of ERK-5 RNA in an individual, as compared to normal levels, may indicate the presence of muscular disease or diabetes mellitus. The ERK-5 probes may further be used to assay cellular factor activity in general and specifically in muscle tissue.

V. A Kit for Detecting the Presence of ERK-5 in a Sample.

In another embodiment, the present invention relates to a kit for detecting the presence of ERK-5 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising a ERK-5 Nucleic Acid Molecule and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecules.

In another embodiment, the present invention relates to a nucleic acid molecule comprising a transcriptional region functional in a cell, a sequence complimentary to an RNA sequence encoding an amino acid sequence corresponding to the above-described polypeptide, and a transcriptional termination region functional in said cell.

Preferably, the above-described molecules are isolated and/or purified DNA molecules.

In another embodiment, the present invention relates to a cell or organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at lower levels.

One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an ERK-5 gene may be obtained by the above-described methods. This region may be retained for its transcriptional termination regulatory sequences, such as termination and polyadenylation. Thus, by retaining the 3'-region naturally contiguous to the DNA sequence encoding an ERK-5 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an ERK-5 sequence) are said to be operably linked if the nature of the linkage between the two DNA sequences does not (1) result in the introduction of a frame-shift mutation, (2) interfere with the ability of the promoter region sequence to direct the transcription of an ERK-5 gene sequence, or (3) interfere with the ability of the an ERK-5 gene sequence to be transcribed by the promoter region sequence. Thus, a promoter region would be operably linked to a DNA sequence if the promoter were capable of effecting transcription of that DNA sequence.

Thus, to express an ERK-5 gene, transcriptional and translational signals recognized by an appropriate host are necessary.

The present invention encompasses the expression of the ERK-5 gene (or a functional derivative thereof) in either prokaryotic or eukaryotic cells. Prokaryotic hosts are, generally, very efficient and convenient for the production of recombinant proteins and are, therefore, one type of preferred expression system for the ERK-5 gene.

Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express ERK-5 (or a functional derivative thereof) in a prokaryotic cell, it is necessary to operably link the ERK-5 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the δ-28-specific promoters of *B. subtills* (Gilman et al., *Gene sequence* 32:11–20 (1984)), the promoters of the bacteriophages of Bacillus (Gryczan, In: *The Molecular Biology of the Bacilli*, Academic Press, Inc., New York (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the ERK-5 peptide of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K 1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example the Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of ERK-5 in insects cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out posttranslational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of ERK-5.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of ERK-5 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes ERK-5 (or a functional derivative thereof) does not contain any intervening codons which are capable of encoding a methionine (i.e., AUG). The presence of such codons results either in a formation of a fusion protein (if the AUG codon is in the same reading frame as the ERK-5 coding sequence) or a frame-shift mutation (if the AUG codon is not in the same reading frame as the ERK-5 coding sequence).

An ERK-5 nucleic acid molecule and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual,* second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan. (In: *The Molecular Biology of the Bacilli,* Academic Press, New York (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology,* Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 9:265–274 (1982); Broach, In: *The Molecular Biology of the Yeast Saccharomyces: Life Cycle and Inheritance,* Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise,* Vol. 3, Gene Sequence Expression, Academic Press, New York, pp. 563–608 (1980)).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of ERK-5 or fragments thereof. This can take place in the transformed cells as such, or following the induction of these cells to differentiate (for example, by administration of bromodeoxyuracil to neuroblastoma cells or the like).

A variety of incubation conditions can be used to form the peptide of the present invention. The most preferred conditions are those which mimic physiological conditions.

VII. An Antibody Having Binding Affinity to an ERK-5 Polypeptide, or a Binding Fragment Thereof and a Hybridoma Containing the Antibody.

In another embodiment, the present invention relates to an antibody having binding affinity to an ERK-5 polypeptide, or a binding fragment thereof. In a preferred embodiment, the polypeptide has the amino acid sequence set forth in SEQ ID NO:2, or mutant or species variation thereof, or at least 9 contiguous amino acids thereof (preferably, at least 10, 15, 20, or 30 contiguous amino acids thereof).

In another preferred embodiment, the present invention relates to an antibody having binding affinity to an ERK-5 polypeptide, or a binding fragment thereof and not to ERK-1, ERK-2, ERK-3, or ERK-4. Such an antibody may be isolated by comparing its binding affinity to ERK-5 with its binding affinity to ERK-1, ERK-2, ERK-3, or ERK-4. Those which bind selectively to ERK-5 would be chosen for use in methods requiring a distinction between ERK-5 and ERK-1, ERK-2, ERK-3, or ERK-4 polypeptides. Such methods could include, but should not be limited to, the analysis of altered ERK-5 expression in tissue containing ERK-1, ERK-2, ERK-3, or ERK-4.

The ERK-5 proteins of the present invention can be used in a variety of procedures and methods, such as for the generation of antibodies, for use in identifying pharmaceutical compositions, and for studying DNA/protein interaction.

The ERK-5 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

In another embodiment, the present invention relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, *"Monoclonal Antibody Technology: Laboratory Techniques in Biochemistry and Molecular Biology,"* Elsevier Science Publishers, Amsterdam, The Netherlands (1984); St. Groth et at., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology, supra* (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be delectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *"Handbook of Experimental Immunology"* 4th Ed., Blackwell Scientific Publications, Oxford, England, Chapter 10 (1986); Jacoby et al., *Meth. Enzym.* 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide,* W. H. Freeman, New York, pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the ERK-5 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting an ERK-5 Polypeptide in a Sample.

In another embodiment, the present invention relates to a method of detecting an ERK-5 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of ERK-5 in a sample as compared to normal levels may indicate muscular disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *"An Introduction to Radioimmunoassay and Related Techniques"* Elsevier Science Publishers, Amsterdam, The Netherlands (1986); Bullock et al., *"Techniques in Immunocytochemistry,"* Academic Press, Orlando, Fla. Vol. 1 (1982), Vol. 2 (1983), Vol. 3 (1985); Tijssen, *"Practice and Theory of Enzyme Immunoassays: Laboratory Techniques in Biochemistry and Molecular Biology,"* Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising Antibodies to ERK-5.

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the antibody. The compartmentalized kit may be as described above for nucleic acid probe kits.

One skilled in the art will readily recognize that the antibodies described in the present invention can readily be incorporated into one of the established kit formats which are well known in the art.

X. Isolation of Compounds Which Interact With ERK-5

In another embodiment, the present invention relates to a method of detecting a compound capable of binding to ERK-5 or a fragment thereof comprising incubating the compound with ERK-5 or fragment thereof and detecting the presence of the compound bound to ERK-5 or fragment thereof. In a preferred embodiment, the compound is present within a complex mixture, for example, serum, body fluid, or cell extracts.

In another embodiment, the present invention relates to a method of detecting an agonist or antagonist of ERK-5 activity comprising incubating cells that produce ERK-5 in the presence of a compound and detecting changes in the level of ERK-5 activity. The compounds thus identified would produce a change in activity indicative of the presence of the compound. In a preferred embodiment, the compound is present within a complex mixture, for example, serum, body fluid, or cell extracts. Once the compound is identified it can be isolated using techniques well known in the art.

In a further embodiment, the present invention relates to a method of agonizing (stimulating) or antagonizing ERK-5 associated activity in a mammal comprising administering to said mammal an agonist or antagonist to ERK-5 in an amount sufficient to effect said agonism or antagonism. In a preferred embodiment, the present invention relates to a possible method of treating diabetes mellitus, skeletal muscle diseases, Alzheimer's disease, or peripheral neuropathies in a mammal with an agonist or antagonist of ERK-5 activity comprising administering the agonist or antagonist to a mammal in an amount sufficient to agonize or antagonize ERK-5 associated functions. Further, since ERK-5 is preferentially expressed in skeletal muscle, the agonist or antagonist might be used in normal individuals.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg, preferably 0.1 mg/kg to 1.0 mg/kg, of the agonist or antagonist of the invention, in one or more administrations daily, for one or several days. The agonist or antagonist can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science,* 16th Ed., Mack Eds. (1980).

In another embodiment, the present invention relates to a pharmaceutical composition comprising the above described ERK-5 agonist or antagonist in an amount sufficient to alter ERK-5 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton Pa. (1980) and WO 91/19008).

The present invention is described in further detail in the following non-limiting examples.

Example 1

Screening of a Human Skeletal Muscle cDNA Library with Radiolabelled Oligonucleotides Total RNA was isolated from human skeletal muscle by the acid guanidinium thiocyanate-phenol-chloroform extraction procedure as described by Puissant et al., *Bio Techniques* 8:148–149 (1990). Poly (A+) RNA was isolated on an oligo(dT) column (Avid et al., *Proc. Natl. Acad. Sci. USA* 69:1408–1412 (1972)). A cDNA library was constructed using the methods described by Okayama and Berg, *Mol. Cell. Biol.* 2:161–170 (1982); Okayama and Berg, *Mol. Cell. Biol.* 3:280–289 (1983). The pCDVI-PL vector was used for preparation of the primer fragment (Noma et al., *Nature* 319:640–646 (1986)). A short synthetic adapter was used as second strand primer as recently described (Boel, E. et al., *Bio Techniques* 11 (1):26–28 (July, 1991)). *E. coli* DH5α (Gibco BRL, Gaithersburg, Md. 20877, USA) was used for transformation according to the protocols by H. Inuoue et al., *Gene* 96:23–28 (1990). After transformation, the bacteria were plated on LB plates containing 50 µg/ml ampicillin at a density of about 8000 colonies per 15 cm plate. Nitrocellulose replica filters (Schleicher & Schuell, BA85) were screened with standard colony hybridization technique (Sambrook et al., *Molecular Cloning: A Laboratory Manual*, Cold Spring Harbor, N.Y. 1989). An equimolar mixture of the following three oligonucleotides which were labelled at the 5' end using T4 polynucleotide kinase and [γ-$^{32}$P] ATP (Amersham, Braunschweig) (Sambrook et al., 1989) was used for hybridization.

filters and allowed to hybridize at 42° C. for 2 h. The filters were washed in 6×SSC, 0.05% SDS three times 10 min first at room temperature, then at 42°, 46°, 48° and 50° C., respectively.

Two positive clones were identified by autoradiography and isolated following the procedure described in Sambrook et al., 1989. Partial dideoxy sequencing (Sanger et al., *Proc. Natl. Acad. Sci. USA* 74:5463–5467 (1977)) of the two positive clones using oligonucleotide E13 as primer revealed identical nucleotide sequence. The larger clone with an insert of about 1900 bp was then fully sequenced. The first methionine precedes an open reading frame of 1179 bp encoding a protein of 393 amino acids (FIG. 1, SEQ ID NO:1 and SEQ ID NO:2) or 43.2 kD molecular weight which shows 61% similarity (38% identity) to the human ERK1 peptide sequence, 64% similarity to the rat ERK1 and ERK2 (39% and 37% identity, respectively) and 55% similarity to the rat ERK3 (30% identity) (the comparison program uses the algorithm of Needleman and Wunsch, *J. Mol. Biol.* 48:443–453 (1970)). The new clone was termed human ERK5 (hERK5).

Example 2

Northern Blot Analysis of Human ERK5

Total RNA from human tissue was isolated by the acid guanidinium thiocyanate-phenol-chloroform extraction procedure (Puissant and Houdebine, *BioTechniques* 8:148–149 (1990)). The preparation of poly(A+) RNA was performed as described by Aviv and Leder, *Proc. Natl. Acad. Sci. USA* 69:1408–1412 (1972). Five µg of poly(A+) RNA per lane were loaded on a 1.2% agarose-2.2M formaldehyde gel and after separation blotted onto a nitrocellulose filter using standard techniques (Sambrook et al., 1989).

A $^{32}$P labelled 1200 bp BamHI fragment of hERK5 in 30 ml of hybridization solution (5× Denhardt's solution, 5×SSC, 5 µg/ml salmon sperm DNA, 50 mM Na$_2$HPO$_4$ pH 6.8, 1 mM NaH$_2$PO$_4$/Na$_4$P$_2$O$_4$, 50% formamide) was used for hybridization. The $^{32}$P labelling was done using the Random primed DNA labelling kit (Bat No. 1004760,

| E10 | 5' AAG GGT TTT ACC ATG GCA GAG AAA 3' | SEQ ID NO:3 |
|---|---|---|
| | Met Ala Glu Lys | |
| E11 | 5' TTA ACT TGT CGA CTA CGT CAG CAG 3' | SEQ ID NO:5 |
| E13 | 5' A(CT) AT(GT) TGG (GT)CT G(CT) (AG) GGC TGC ATC 3' | SEQ ID NO:6 |

The nucleotide sequences of the oligonucleotides correspond to nucleotides (nt) 378–401 (E10, including the first in frame methioninecodon) and nt 2033–2010 (E11, reverse primer, including the first in frame stop codon), respectively, of the rat ERK-3 sequence published by Boulton et al., *Cell* 65:663–675 (1991) with single modifications outside the coding region to introduce new restriction sites (NcoI in E10 and SalI in E11, respectively). E13 was designed as 32 fold degenerate oligonucleotide based on the amino acid sequence of rat ERK1, ERK2 and ERK3 corresponding to nt 1030–1052 of rat erk3 (Boulton et al., *Cell* 65:663–675 (1991)).

A total of 10 pmoles of the labelled oligonucleotides E10, E11 and E13 in 50 ml hybridization mixture (6×SSC, 5× Denhardt's solution, 0.05% SDS (*Current Protocols in Molecular Biology*, M. Ausubel et al., eds., John Wiley & Sons, New York (1988)) were added to replica nitrocellulose Boehringer Mannheim Biochemica) according to the manufacturers instruction. Fifty ng of denatured DNA were labelled with 50 µCi $^{32}$PdATP with an average incorporation of $2 \times 10^8$–$10^9$ cpm/µg DNA. After the labelling reaction unincorporated $^{32}$PdATP was removed using a Sephadex G50 column. The washed filter was exposed to an X-ray film. Analysis of the Northern Blot showed that there is a major transcript of hERK5 of about 1.9 kb (FIG. 2). Further, it appears that hERK5 is preferentially expressed in skeletal muscle.

Example 3

Production of Polyclonal Antibodies Against hERK5

Figure 3:
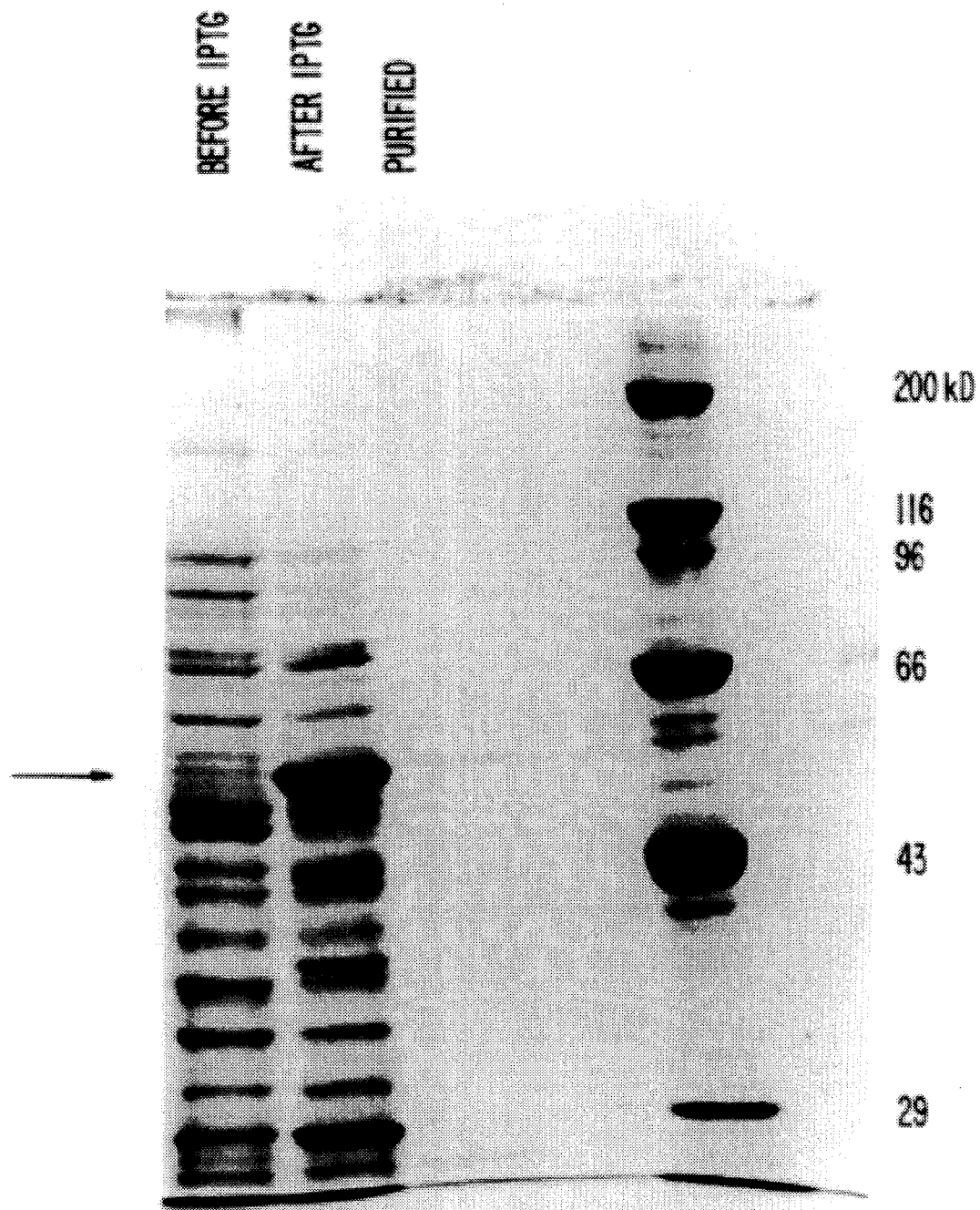
FIG. 3. hERK5-GST fusion protein expression in *E. coli* (Coomassie Blue Staining).

Antibodies were raised against an *E. coli* fusion protein composed of the carboxy-terminal part of glutathione S-transferase and the last 264 amino acids of hERK5 protein. The vector encoding this construct was generated by cloning a 1200 bp BamHI-fragment of hERK5 into the pGEX3X plasmid (Pharmacia, Uppsala) which upstream of the multiple cloning site carries the cDNA for about 250 amino acids (27.5 kD) of glutathione S-transferase under the control of the lac promoter. The construct was transformed in *E. coli* 298F' cells (R. du Bridge, Genentech, San Francisco). After induction with IPTG (1 mM final concentration) the expressed soluble fusion protein was purified on Glutathione-Sepharose 4B (Pharmacia, Uppsala) according to the manufacturer's instruction. The apparent molecular weight in SDS-PAGE is 56 kD (FIG. 3). The purified fusion protein (100 μg) was subcutaneously injected into a female rabbit using Freund's adjuvant as described in Harlow and Lane, *Antibodies: A Laboratory Manual,* Cold Spring Harbor, N.Y. (1988). After the second boost, antiserum was collected and used in Western blotting.

Figure 4:
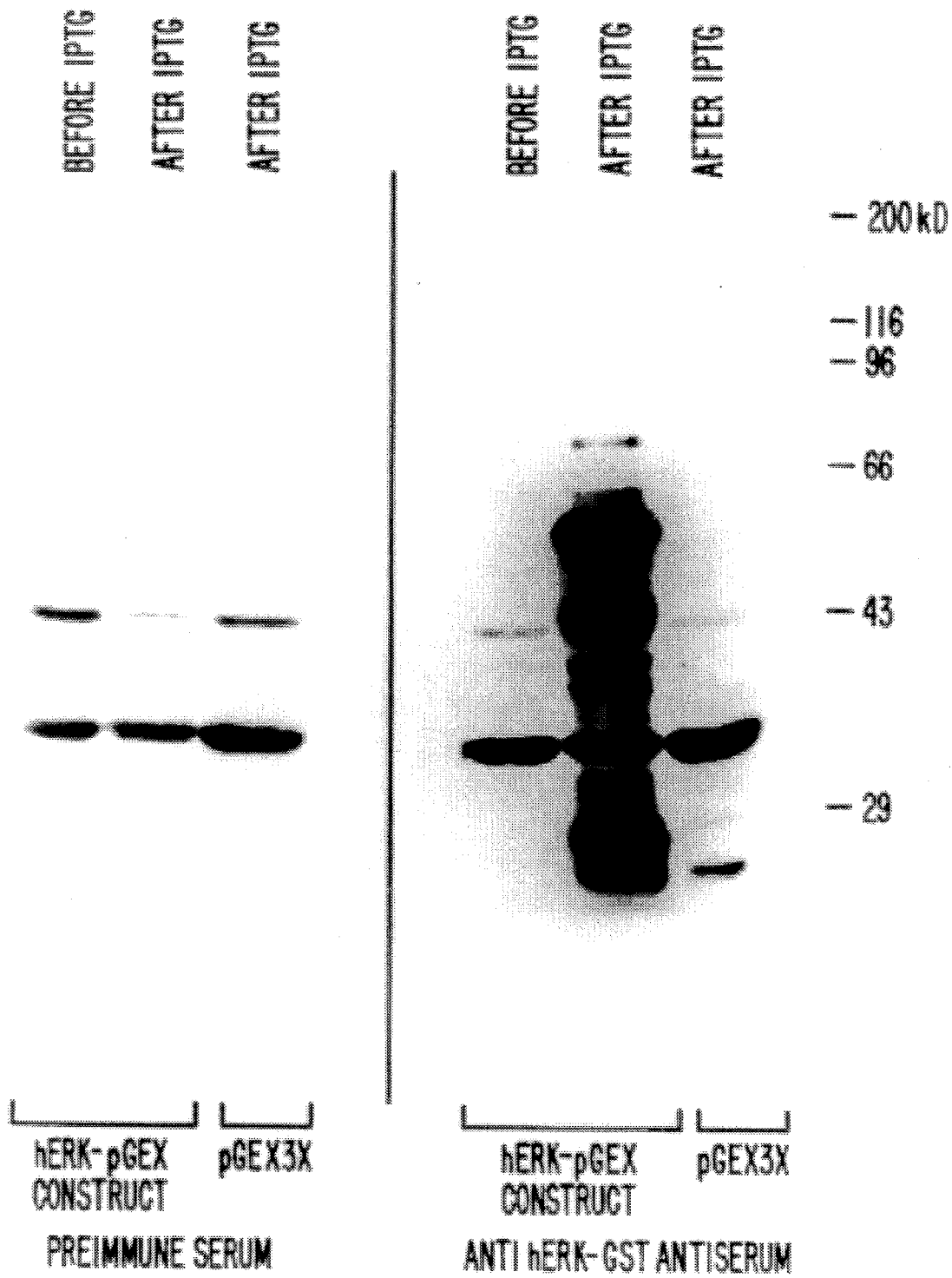
FIG. 4. Western blot of total lysates from *E. coli* expressing hERK5-GST fusion protein or GST protein (control).

For Western blotting total lysate of *E. coli* clones expressing either the pGEX encoded GST protein portion or the hERK-5-GST fusion protein before and after induction with IPTG was separated on SDS-PAGE. The bacteria were harvested by centrifugation and resuspended in Laemmli sample buffer (4% SDS, 125 mM Tris pH 6.8, 10% β-mercapto ethanol, 10% glycerol, 0.02% bromphenol blue) to a concentration of $2 \times 10^7$ cells/μl of sample buffer. After boiling for 5 min, 10 μl pd of this SDS lysate were applied to SDS-PAGE (10% polyacrylamide), transferred to nitrocellulose using standard techniques (Sambrook et al., (1989), 200 mA, 40 min), blocked with PBS containing 2% nonfat dry milk, 0.02% Tween20, washed (PBS 0.02% Tween 20, 0.2% gelatine) and detected with the polyclonal antiserum raised against the hERK-GST fusion protein in comparison to preimmune serum (both sera diluted 1:5000 in PBS containing 0.05% Tween 20 and 0.2% gelatine). The second antibody (horseradish peroxidase coupled goat anti-rabbit IgG (BioRad, MCtnchen)) was diluted 1:20000 fold in PBS 0.02% Tween 20, 0.2% gelatine. Peroxidase reaction was performed using the ECL kit (Amersham, Braunschweig). The antiserum strongly recognizes a band at 56 kD corresponding to the molecular weight of the hERK-GST fusion protein which is not detected by the preimmune serum. There is no cross reactivity of the anti-hERK-5-GST antiserum with the recombinant GST protein portion (FIG. 4).

Example 4

Expression of hERK5 in Eukaryotic Cells

The herk5 cDNA was cloned in the eukaryotic expression vector pcDNAI (Invitrogen, San Diego) and hERK-5 was transiently expressed in human embryonal kidney fibroblasts (293 cells:ATCC CRL 1573). The 293 cells were grown in DMEM with 4.5 mg/ml glucose and 10% FCS. $5 \times 10^4$ cells per 3.5 cm dish were transfected with 10 μg DNA using the calcium-phosphate precipitation method described by Chen and Okayama (*Mol. Cell. Biol.* 7:2745–2752 (1987)). After 16 h at 35° C. and 3% $CO_2$ the medium was changed. The cells were transferred to 37° C. and 5% $CO_2$ for additional 16 h, washed off the cultured dish, collected by centrifugation, and resuspended in Laemmli sample buffer (composition see Example 3, 40 μl per 3.5 cm dish).

Figure 5:
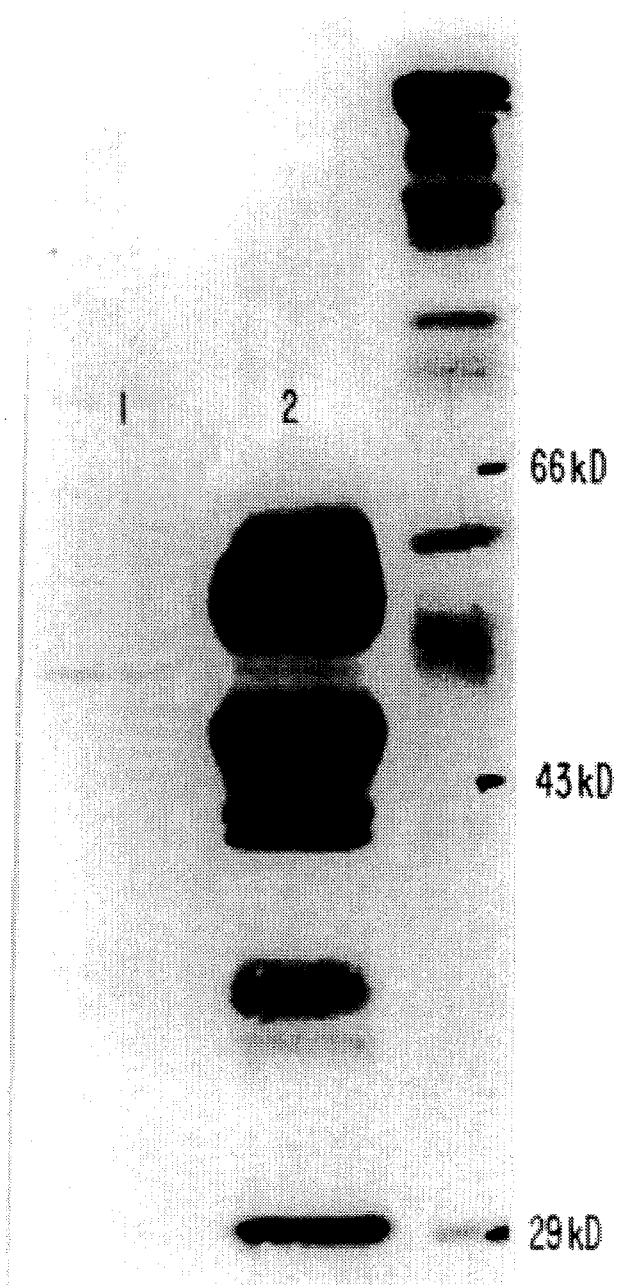
FIG. 5. Expression of hERK5 in 293 cells. Lane 1: 293 cells transfected with pcDNAI vector. Lane 2: 293 cells transfected with hERK5-pcDNAI construct.

The Western blot of 293 cell SDS-lysate after pcDNAI-herk5 transfection shows major bands at 44 kD (which corresponds to the predicted molecular weight of hERK5) and 46 kD, probably representing a different phosphorylation state of hERK5 protein (FIG. 5). There is no cross reactivity with proteins expressed in mock transfected 293 cells.

Example 5

Generation of Stable Cell Lines Expressing hERK5

NIH3T3 cells, immortalized mouse fibroblasts (Jainchill et al., *J. Virol.* 4:549–553 (1969)) were grown in DMEM with 4.5 mg/ml glucose and 10% FCS to subconfluency and transfected with 20 μg/$1 \times 10^7$ cells of a cvn-construct containing the complete hERK-5 cDNA. The cvn vector carries the SV40 early promoter, HBV poly A signal as well as a neomycin resistance gene which allows selection of transfected cells on G418 resistance, and the gene for the DHFR which can be used to increase the expression of the integrated cDNA by addition of methotrexate at concentrations of 100–1000 nM to the culture medium (Rosenthal et al., *Cell* 46:155–169 (1986)). Transfection was performed as described in Example 4. After 16 h at 35° C. and 3% $CO_2$, the medium was changed and the cells were grown at 37° C., 5% $CO_2$ for additional 24 h with one medium change after 8 h. The cells were then split to different dilutions and grown in 1 mg/ml G418 containing medium until cell colonies appeared which were isolated and selected on methotrexate growth.

Figure 6:
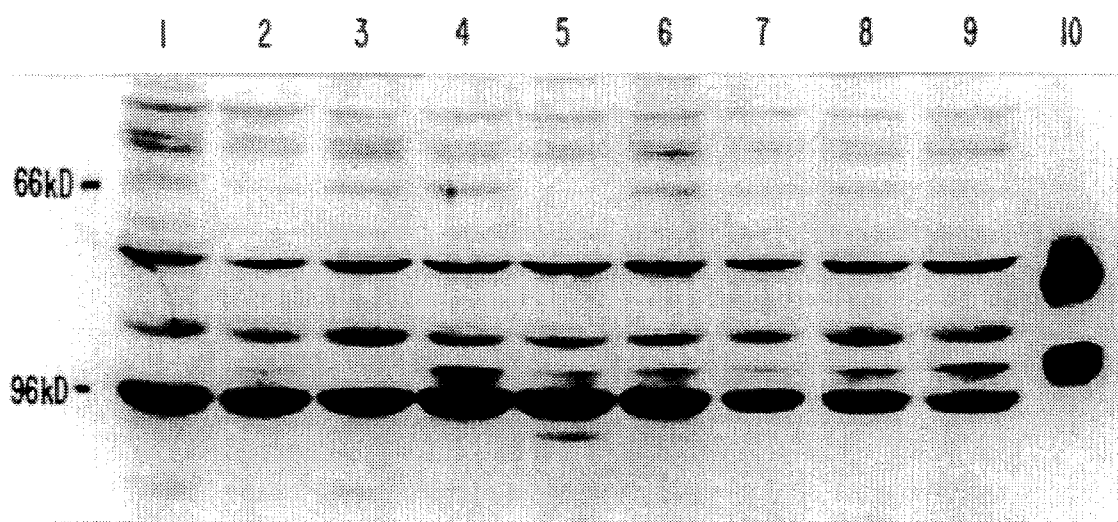
FIG. 6. Stable cell lines expressing hERK5. Lane 1: untransfected NIH 3T3 cells. Lanes 2–5: NIH 3T3 cell clones transfected with the cvn-hERK-5 construct growing in the presence of 100 nM methotrexate. Lane 6: Cell clone of lane 5, 100 nM methotrexate. Lanes 7–8: Cell clone of lane 5, 200 nM methotrexate. Lane 9: Cell clone of lane 5,500 nM methotrexate. Lane 10: Cell lysate of 293 cells transfected with pcDNAI-hERK-5 construct.

The expression of hERE was tested in the Western blot of total cell lysate using the antibody raised against the hERK-5-GST fusion protein as described in Example 3. The blot shows a double band at 44/46 kD in three of four cell clones tested corresponding to the stably expressed hERK5 protein whose expression is increased when the cells are grown on 200 and 500 nM methotrexate, respectively (FIG. 6).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid molecule encoding a polypeptide having an amino acid sequence of at least 9 contiguous amino acids of an amino acid sequence set forth in SEQ ID NO: 2.

2. The isolated nucleic acid molecule according to claim 1, wherein the molecule encodes a polypeptide having an amino acid sequence of at least 15 contiguous amino acids of an amino acid sequence set forth in SEQ ID NO:2.

3. The isolated nucleic acid molecule according to claim 2, wherein the molecule encodes a polypeptide having at least 20 contiguous amino acids of the amino acid sequence set forth in SEQ ID NO:2.

4. The isolated nucleic acid molecule according to claim 3, wherein the molecule encodes a polypeptide having at least 30 contiguous amino acids of the amino acid sequence set forth in SEQ ID NO:2.

5. The isolated nucleic acid molecule according to claim 4, wherein the molecule encodes a polypeptide having a full length ERK-5 amino acid sequence set forth in SEQ ID NO:2.

6. A nucleic acid probe able to detect the presence of ERK-5 nucleic acid in a sample comprising an isolated nucleic acid molecule having at least 27 contiguous nucleotides of a nucleic acid sequence set forth in SEQ ID NO:1.

7. The nucleic acid probe according to claim 6, wherein the isolated nucleic acid molecule has at least 30 contiguous nucleotides of the nucleic acid sequence set forth in SEQ ID NO:1.

8. The nucleic acid probe according to claim 7, wherein the isolated nucleic acid molecule has at least 35 contiguous nucleotides of the nucleic acid sequence set forth in SEQ ID NO:1.

9. The nucleic acid probe according to claim 8, wherein the isolated nucleic acid molecule has at least 40 contiguous nucleotides of the nucleic acid sequence set forth in SEQ ID NO:1.

10. The nucleic acid probe according to claim 9, wherein the isolated nucleic acid molecule has at least 50 contiguous nucleotides of the nucleic acid sequence set forth in SEQ ID NO:1.

11. The nucleic acid probe according to claim 10, wherein the isolated nucleic acid molecule has the entire nucleic acid sequence set forth in SEQ ID NO:1.

12. A nucleic acid probe comprising an isolated nucleic acid encoding a polypeptide having an amino acid sequence of at least 9 contiguous amino acids of an amino acid sequence set forth in SEQ ID NO: 2.

13. A kit for detecting the presence of ERK-5 RNA in a sample comprising at least one container means having disposed therein a nucleic acid probe comprising an isolated nucleic acid encoding a polypeptide having an amino acid sequence of at least 9 contiguous amino acids of an amino acid sequence set forth in SEQ ID NO: 2.

14. A method of detecting ERK-5 RNA in a sample comprising:
    a) contacting said sample with an isolated nucleic acid molecule having at least 27 contiguous nucleotides of a nucleic acid sequence set forth in SEQ ID NO:1, under conditions such that hybridization occurs, and
    b) detecting the presence of said molecule bound to ERK-5 RNA.

15. An isolated nucleic acid molecule comprising, 5' to 3', a promoter effective to initiate transcription in a host cell and a nucleic acid encoding a polypeptide having an amino acid sequence of at least 9 contiguous amino acids of an amino acid sequence set forth in SEQ ID NO: 2.

16. An isolated nucleic acid molecule comprising a vector and a nucleic acid encoding a polypeptide having an amino acid sequence of at least 9 contiguous amino acids of an amino acid sequence set forth in SEQ ID NO: 2.

17. An isolated nucleic acid molecule consisting of a promoter region functional in a cell, a sequence complimentary to an RNA sequence encoding an amino acid sequence corresponding to a polypeptide of at least 9 contiguous amino acids of an amino acid sequence set forth in SEQ ID NO: 2, and a transcription termination region functional in said cell.

18. A transformed cell that contains the isolated nucleic acid molecule according to any one of claims 15, 16, or 17.

\* \* \* \* \*

UNITED STATES PATENT AND TRADEMARK OFFICE
CERTIFICATE OF CORRECTION

PATENT NO. : 5,459,036

DATED : October 17, 1995

INVENTOR(S) : Cornelia Lechner, et al.

It is certified that error appears in the above-indentified patent and that said Letters Patent is hereby corrected as shown below:

Column 1, Line 60: delete "37 %" and insert --37%--.

Column 1, Line 60: delete "55 %" and insert --55%--.

Column 6, Line 48: insert --I.-- in front of "Isolated".

Column 12, Line 17: delete "δ" and insert -- ς --.

Column 12, Line 24: delete "(1987);" and insert --(1987));--.

Column 12, Line 53: delete "CHO-K 1" and insert --CHO-K1--.

Column 13, Line 12: delete "posttranslational" and insert --post-translational--.

Column 14, Line 53: delete "9:265" and insert --19:265--.

Column 15, Line 58: delete "Ansterdam" and insert --Amsterdam--.

Column 17, Line 62: insert --labeled-- in front of "antibody".

Column 18, Line 27: delete "possible".

Column 20, Line 45: insert --SEQ ID NO:4--.

Column 20, Line 53: delete "$10^9$" and insert -- $-1 \times 10^9$ --.

Column 21, Line 25: delete "pd".

UNITED STATES PATENT AND TRADEMARK OFFICE
CERTIFICATE OF CORRECTION

PATENT NO. : 5,459,036
DATED : October 17, 1995
INVENTOR(S) : Cornelia Lechner, et al.

It is certified that error appears in the above-indentified patent and that said Letters Patent is hereby corrected as shown below:

Column 21, Line 35: delete "MCtnchen" and insert --München--.

Column 22, Line 39: delete "hERE" and insert --hERK5--.

Signed and Sealed this

Twenty-first Day of October 1997

Attest:

BRUCE LEHMAN

Attesting Officer  Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1260 base pairs
        ( B ) TYPE: nucleic acid 5,459,036

-continued ( C ) STRANDEDNESS: single
( D ) TOPOLOGY: linear ( i x ) FEATURE:
( A ) NAME/KEY: CDS
( B ) LOCATION: 34..1215

( x i ) SEQUENCE DESCRIPTION: SEQ ID NO:1:

```
GGCTCTGCGG GGTGGGCAGC TCCCGGGCCT GCC ATG AGC TCT CCG CCG CCC GGN       54
                                    Met Ser Ser Pro Pro Pro Gly
                                     1               5

GGC AGT GGC TTT TAC CGC CAG GAG GTG ACC AAG ACG GCC TGG GAG GTG      102
Gly Ser Gly Phe Tyr Arg Gln Glu Val Thr Lys Thr Ala Trp Glu Val
         10              15                  20

CGC GCC GTG TAC CGG GAC CTG CAG CCC GTG GGC TCG GGC GCC TAC GGC      150
Arg Ala Val Tyr Arg Asp Leu Gln Pro Val Gly Ser Gly Ala Tyr Gly
     25              30                  35

GCG GTG TGC TCG GCC GTG GAC GGC CGC ACC GGC GCT AAG GTT GCC ATC      198
Ala Val Cys Ser Ala Val Asp Gly Arg Thr Gly Ala Lys Val Ala Ile
 40              45                  50                      55

AAG AAG CTG TAT CGG CCC TTC CAG TCC GAG CTG TTC GCC AAG CTC GCC      246
Lys Lys Leu Tyr Arg Pro Phe Gln Ser Glu Leu Phe Ala Lys Leu Ala
                 60                  65                  70

TAC CGC GAG CTG CGC CTG CTC AAG CAC ATG CGC CAC GAG AAC GTG ATC      294
Tyr Arg Glu Leu Arg Leu Leu Lys His Met Arg His Glu Asn Val Ile
             75                  80                  85

GGG CTG CTG GAC GTA TTC ACT CCT GAT GAG ACC CTG GAT GAC TTC ACG      342
Gly Leu Leu Asp Val Phe Thr Pro Asp Glu Thr Leu Asp Asp Phe Thr
         90                  95                 100

GAC TTT TAC CTG GTG ATG CCG TTC ATG GGC ACC GAC CTG GGC AAG CTC      390
Asp Phe Tyr Leu Val Met Pro Phe Met Gly Thr Asp Leu Gly Lys Leu
    105                 110                 115

ATG AAA CAT GAG AAG CTA GGC GAG GAC CGG ATC CAG TTC CTC GTG TAC      438
Met Lys His Glu Lys Leu Gly Glu Asp Arg Ile Gln Phe Leu Val Tyr
120                 125                 130                 135

CAG ATG ATG AAG GGG CTG AGG TAT ATC CAC GCT GCC GGC ATC ATC CAC      486
Gln Met Met Lys Gly Leu Arg Tyr Ile His Ala Ala Gly Ile Ile His
                140                 145                 150

AGA GAC CTG AAG CCC GGC AAC CTG GCT GTG AAC GAA GAC TGT GAG CTG      534
Arg Asp Leu Lys Pro Gly Asn Leu Ala Val Asn Glu Asp Cys Glu Leu
            155                 160                 165

AAG ATC CTG GAC TTC GGC CTG GCC AGG CAG GCA GAC AGT GAG ATG ACT      582
Lys Ile Leu Asp Phe Gly Leu Ala Arg Gln Ala Asp Ser Glu Met Thr
        170                 175                 180

GGG TAC GTG GTG ACC CGG TGG TAC CGG GCT CCC GAG GTC ATC TTG AAT      630
Gly Tyr Val Val Thr Arg Trp Tyr Arg Ala Pro Glu Val Ile Leu Asn
185                 190                 195

TGG ATC GCG TAC ACG CAG ACG GTG GAC ATC TGG TCT GTG GGC TGC ATC      678
Trp Ile Ala Tyr Thr Gln Thr Val Asp Ile Trp Ser Val Gly Cys Ile
200                 205                 210                 215

ATG GCG GAG ATG ATC ACA GGC AAG ACG CTG TTC AAG GGC AGC GAC CAC      726
Met Ala Glu Met Ile Thr Gly Lys Thr Leu Phe Lys Gly Ser Asp His
                220                 225                 230

CTG GAC CAG CTG AAG GAG ATC ATG AAG GTG ACG GGG ACG CCT CCG GCT      774
Leu Asp Gln Leu Lys Glu Ile Met Lys Val Thr Gly Thr Pro Pro Ala
            235                 240                 245

GAG TTT GTG CAG CGG CTG CAG AGC GAT GAG GCC AAG AAC TAC ATG AAG      822
Glu Phe Val Gln Arg Leu Gln Ser Asp Glu Ala Lys Asn Tyr Met Lys
        250                 255                 260

GGC CTC CCC GAA TTG GAG AAG AAG GAT TTT GCC TCT ATC CTG ACC AAT      870
Gly Leu Pro Glu Leu Glu Lys Lys Asp Phe Ala Ser Ile Leu Thr Asn
```

|                                                                                                          |      |
|----------------------------------------------------------------------------------------------------------|------|
| GCA AGC CCT CTG GCT GTG AAC CTC CTG GAG AAG ATG CTG GTG CTG GAC                                          | 918  |
| Ala Ser Pro Leu Ala Val Asn Leu Leu Glu Lys Met Leu Val Leu Asp                                          |      |
| 280             285                 290                 295                                              |      |
| GCG GAC ATC AGG TTG ACT GCA GGC GAG TTT CTT TCC CAT CCC TAC TTC                                          | 966  |
| Ala Asp Ile Arg Leu Thr Ala Gly Glu Phe Leu Ser His Pro Tyr Phe                                          |      |
|                 300                 305                 310                                              |      |
| GAG TCC CTG CAC GAC ACG GAA GAT GAG CCC CAG GTC CAG AAG TAT GAT                                          | 1014 |
| Glu Ser Leu His Asp Thr Glu Asp Glu Pro Gln Val Gln Lys Tyr Asp                                          |      |
|             315                 320                 325                                                  |      |
| GAC TCC TTT GAC TAC TTT GAC CGC ACA CTG GAT GAA TGG AAG CCG TGT                                          | 1062 |
| Asp Ser Phe Asp Tyr Phe Asp Arg Thr Leu Asp Glu Trp Lys Pro Cys                                          |      |
|         330                 335                 340                                                      |      |
| TAC TTA CAA AGA GGT GCT CAG CTT CAA GCC TCC CCG GCA GCT GGG GGC                                          | 1110 |
| Tyr Leu Gln Arg Gly Ala Gln Leu Gln Ala Ser Pro Ala Ala Gly Gly                                          |      |
|     345                 350                 355                                                          |      |
| CAG GGT CTC CAA GGA GAC GCC TCT GTG AAG ATC TCT GGG CTC CGG GGT                                          | 1158 |
| Gln Gly Leu Gln Gly Asp Ala Ser Val Lys Ile Ser Gly Leu Arg Gly                                          |      |
| 360                 365                 370                 375                                          |      |
| GGC AGT GAG GAC CAC CTT CAC CTT CCA CCT GAG AGG GGA CTC TCG TTG                                          | 1206 |
| Gly Ser Glu Asp His Leu His Leu Pro Pro Glu Arg Gly Leu Ser Leu                                          |      |
|                 380                 385                 390                                              |      |
| CCA CCT TGACCTTGGC TGGGGCTTGC ATCCCAAGGC ATCCATCAGA GCAGACGC                                             | 1260 |
| Pro Pro                                                                                                  |      |

(2) INFORMATION FOR SEQ ID NO:2:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:2:

| Met | Ser | Ser | Pro | Pro | Pro | Gly | Gly | Ser | Gly | Phe | Tyr | Arg | Gln | Glu | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Lys | Thr | Ala | Trp | Glu | Val | Arg | Ala | Val | Tyr | Arg | Asp | Leu | Gln | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Gly | Ser | Gly | Ala | Tyr | Gly | Ala | Val | Cys | Ser | Ala | Val | Asp | Gly | Arg |
|-----|-----|-----|-----|-----|-----|-----|-----|-----|-----|-----|-----|-----|-----|-----|-----|
|     |     | 35  |     |     |     | 40  |     |     |     |     | 45  |     |     |     |     |

| Thr | Gly | Ala | Lys | Val | Ala | Ile | Lys | Lys | Leu | Tyr | Arg | Pro | Phe | Gln | Ser |
|-----|-----|-----|-----|-----|-----|-----|-----|-----|-----|-----|-----|-----|-----|-----|-----|
|     | 50  |     |     |     | 55  |     |     |     |     | 60  |     |     |     |     |     |

| Glu | Leu | Phe | Ala | Lys | Leu | Ala | Tyr | Arg | Glu | Leu | Arg | Leu | Leu | Lys | His |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Met | Arg | His | Glu | Asn | Val | Ile | Gly | Leu | Leu | Asp | Val | Phe | Thr | Pro | Asp |
|-----|-----|-----|-----|-----|-----|-----|-----|-----|-----|-----|-----|-----|-----|-----|-----|
|     |     |     | 85  |     |     |     |     | 90  |     |     |     |     | 95  |     |     |

| Glu | Thr | Leu | Asp | Asp | Phe | Thr | Asp | Phe | Tyr | Leu | Val | Met | Pro | Phe | Met |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gly | Thr | Asp | Leu | Gly | Lys | Leu | Met | Lys | His | Glu | Lys | Leu | Gly | Glu | Asp |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Ile | Gln | Phe | Leu | Val | Tyr | Gln | Met | Met | Lys | Gly | Leu | Arg | Tyr | Ile |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| His | Ala | Ala | Gly | Ile | Ile | His | Arg | Asp | Leu | Lys | Pro | Gly | Asn | Leu | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Asn | Glu | Asp | Cys | Glu | Leu | Lys | Ile | Leu | Asp | Phe | Gly | Leu | Ala | Arg |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gln | Ala | Asp | Ser | Glu | Met | Thr | Gly | Tyr | Val | Val | Thr | Arg | Trp | Tyr | Arg |
|-----|-----|-----|-----|-----|-----|-----|-----|-----|-----|-----|-----|-----|-----|-----|-----|

|  |  |  | 180 |  |  |  |  | 185 |  |  |  |  | 190 |  |  |
|---|---|---|---|---|---|---|---|---|---|---|---|---|---|---|---|
| Ala | Pro | Glu<br>195 | Val | Ile | Leu | Asn | Trp<br>200 | Ile | Ala | Tyr | Thr | Gln<br>205 | Thr | Val | Asp |
| Ile | Trp<br>210 | Ser | Val | Gly | Cys | Ile<br>215 | Met | Ala | Glu | Met | Ile<br>220 | Thr | Gly | Lys | Thr |
| Leu<br>225 | Phe | Lys | Gly | Ser | Asp<br>230 | His | Leu | Asp | Gln | Leu<br>235 | Lys | Glu | Ile | Met | Lys<br>240 |
| Val | Thr | Gly | Thr | Pro<br>245 | Pro | Ala | Glu | Phe | Val<br>250 | Gln | Arg | Leu | Gln | Ser<br>255 | Asp |
| Glu | Ala | Lys | Asn<br>260 | Tyr | Met | Lys | Gly | Leu<br>265 | Pro | Glu | Leu | Glu | Lys<br>270 | Lys | Asp |
| Phe | Ala | Ser<br>275 | Ile | Leu | Thr | Asn | Ala<br>280 | Ser | Pro | Leu | Ala | Val<br>285 | Asn | Leu | Leu |
| Glu | Lys<br>290 | Met | Leu | Val | Leu | Asp<br>295 | Ala | Asp | Ile | Arg | Leu<br>300 | Thr | Ala | Gly | Glu |
| Phe<br>305 | Leu | Ser | His | Pro | Tyr<br>310 | Phe | Glu | Ser | Leu | His<br>315 | Asp | Thr | Glu | Asp | Glu<br>320 |
| Pro | Gln | Val | Gln | Lys<br>325 | Tyr | Asp | Asp | Ser | Phe<br>330 | Asp | Tyr | Phe | Asp | Arg<br>335 | Thr |
| Leu | Asp | Glu | Trp<br>340 | Lys | Pro | Cys | Tyr | Leu<br>345 | Gln | Arg | Gly | Ala | Gln<br>350 | Leu | Gln |
| Ala | Ser | Pro<br>355 | Ala | Ala | Gly | Gly | Gln<br>360 | Gly | Leu | Gln | Gly | Asp<br>365 | Ala | Ser | Val |
| Lys | Ile<br>370 | Ser | Gly | Leu | Arg | Gly<br>375 | Gly | Ser | Glu | Asp | His<br>380 | Leu | His | Leu | Pro |
| Pro<br>385 | Glu | Arg | Gly | Leu | Ser<br>390 | Leu | Pro | Pro |  |  |  |  |  |  |  |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AAGGGTTTTA CCATGGCAGA GAAA    24

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:4:

Met Ala Glu Lys
  1

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTAACTTGTC GACTACGTCA GCAG    24

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ACTATGTTGG GTCTGCTAGG GCTGCATC                                    2 8